United States Patent [19]

Yamane et al.

[11] Patent Number: 5,601,976
[45] Date of Patent: Feb. 11, 1997

[54] METHOD FOR DETECTING TARGET NUCLEIC ACID IN SPECIMEN

[75] Inventors: Akio Yamane; Takanori Oka; Satoru Nakagami; Kenichi Miyoshi, all of Koda-Cho, Japan

[73] Assignee: Wakunaga Seiyaku Kabushiki Kaisha, Japan

[21] Appl. No.: 945,573

[22] Filed: Sep. 16, 1992

Related U.S. Application Data

[63] Continuation of Ser. No. 415,358, filed as PCT/JP88/01316, Dec. 23, 1988, abandoned.

[30] Foreign Application Priority Data

Dec. 25, 1987 [JP] Japan ................... 62-328785
Jun. 16, 1988 [JP] Japan ................... 63-149157
Sep. 16, 1988 [JP] Japan ................... 63-231737

[51] Int. Cl.$^6$ ............... C12Q 1/68; C07H 21/04; C12P 19/34; C12N 15/00
[52] U.S. Cl. ............ 435/6; 536/24.33; 435/91.2; 935/77; 935/78
[58] Field of Search .............. 435/6, 91, 91.2; 536/24.33; 935/77, 78

[56] References Cited

U.S. PATENT DOCUMENTS

| | | | |
|---|---|---|---|
| 4,683,195 | 7/1987 | Mullis et al. | 435/6 |
| 4,806,546 | 2/1989 | Carrico et al. | 536/25.3 |
| 4,851,331 | 7/1989 | Varey et al. | 435/6 |
| 4,965,188 | 10/1990 | Mullis et al. | 435/6 |
| 4,968,602 | 11/1990 | Dattagupta | 435/6 |

FOREIGN PATENT DOCUMENTS

| | | |
|---|---|---|
| 0194545 | 9/1986 | European Pat. Off. . |
| 0200362 | 11/1986 | European Pat. Off. . |
| 0278220 | 8/1988 | European Pat. Off. . |
| 2169403 | 7/1986 | United Kingdom . |
| 2202328 | 9/1988 | United Kingdom . |

*Primary Examiner*—Mindy B. Fleisher
*Attorney, Agent, or Firm*—Wenderoth, Lind & Ponack

[57] ABSTRACT

An intended nucleic acid is determined in a sample by a method in which at least one of the nucleic acid strands of the intended nucleic acid is subjected to hybridization with a primer and to chain-extension reaction over the primer to form a synthesized nucleic acid which is complementary to and in hybridization with the strand; a copy of the intended nucleic acid is obtained, which copy is (a) the nucleic acid of the double-stranded double produced by the chain-extension reaction, or (b) the synthesized nucleic acid freed from the double-stranded nucleic acid, or (c) a double stranded nucleic acid form from a pair of the synthesized nucleic acids complementary with each other; and it is determined whether the copy is present in the sample thereby to know whether the intended nucleic acid is in present in the sample.

19 Claims, 3 Drawing Sheets

METHOD FOR DETECTING TARGET NUCLEIC ACID IN SPECIMEN

This application is a continuation of now abandoned application Ser. No. 07/415,358, filed as PCT/JP88/01316, Dec. 23, 1988, now abandoned.

FIELD OF THE ART

This invention relates to a method for detecting a base sequence of a specific gene without use of the so-called hybridization method. More particularly, the present invention relates to a method of detecting a nucleic acid which method comprises subjecting (i) a nucleic acid sequence which has been formed by hybridizing the nucleic acid sequence to be detected with at least one primer which is complementary to the nucleic acid sequence to be detected and effecting chain-extending reaction such that unit nucleic acids are added to the primer to form a nucleic acid sequence which is complementary to the nucleic acid sequence to be detected or (ii) a nucleic acid sequence which has a double stranded portion and which has been formed from the nucleic acid sequences each of which is a product of the extending reaction applied to the primer, to (a) isolation by means of a solid-phase separation aid or more particularly to isolation wherein the nucleic acid sequence is immobilized on a solid carrier or to (b) isolation by means of a solid-phase absorbent which has a selective adsorbing capability either to a double stranded nucleic acid or to a single stranded nucleic acid and the unit nucleic acids, and detecting the nucleic acid sequence thus isolated.

BACKGROUND ART

With rapid progress of molecular biology of genes, it has become very important to detect the base sequence of a specific gene. For example, detection of a gene in diagnosis of genetic disease before birth, diagnosis of cancer at molecular level or detection of a pathogen such as virus is seriously significant.

For such detection of genes, the method called hybridization has been employed (B. D. Hames and S. J. Higgins: Nucleic acid hybridization, a practical approach, IRL Press, 1985). This method is a method in which a single stranded DNA or a double stranded DNA having the base sequence complementary to a target sequence is labelled with a radioactive or non-radioactive label, then bound to the target sequence by utilizing the complementarity to the target sequence, namely hybridized with the target sequence to detect the target sequence. In this case, generally, the dot hybridization method to fix the target substance to a carrier [DNA, 4, 327–331, (1985)] or the Southern hybridization method [Molecular Cloning, p. 382, Cold Spring Harbor (1982)], etc. are practiced. However, these methods are cumbersome and require considerable amount of labors, and in spite of the efforts made for mechanical automation, it may be still impossible to analyze a large number of samples as routine works. For overcoming these problems, the hybridization method in which a probe is fixed onto a carrier has been devised [for example, T. R. Gingeras et al: Nucleic Acids Res. 15, 5373–5390], but such hybridization between liquid phase and solid phase is limited, and it cannot have become a method practically applicable with respect to sensitivity, etc. For overcoming the drawbacks of these liquid phase-solid phase hybridizations, the sandwich type liquid phase-liquid phase hybridization has been devised [for example, Ann-Christine Syvaenen et al: Nucleic Acids Res. 14, 5037–5048 (1986), Japanese Laid-Open Patent Publication No. 229068/1987]. However, these methods cannot be satisfactory with respect to high background becasue of use of a large excess of probe or sensitivity.

For improving sensitivity, a method to amplify a specific nucleic acid sequence has been developed (Japanese Laid-Open Patent Publication No. 281/1987) which corresponds to U.S. Pat. Nos. 4,683,195; 4,683,202; and 4,800,159 to Mullis et al. but the operation of hybridization is required also in this method, whereby cumbersomeness is not reduced at all.

DISCLOSURE OF THE INVENTION

It is an object of the present invention is to solve the problems given hereinabove thereby to present a method of detecting a specific nucleic acid with ease and in high sensitivity.

This object is attained by the method which comprises subjecting (i) a nucleic acid sequence which has been formed by hybridizing the nucleic acid sequence to be detected with at least one primer which is complementary to the nucleic acid sequence to be detected and effecting chain-extending reaction such that unit nucleic acids are added to the primer to form a nucleic acid sequence which is complementary to the nucleic acid sequence to be detected or (ii) a nucleic acid sequence which has a double stranded portion and which has been formed from the nucleic acid sequences each of which is a product of the extending reaction applied to the primer, to (a) isolation by means of a solid-phase separation aid or more particularly to isolation wherein the nucleic acid sequence is immobilized on a solid carrier or to (b) isolation by means of a solid-phase absorbent which has a selective adsorbing capability either to a double stranded nucleic acid or to a single stranded nucleic acid and the unit nucleic acids, and detecting the nucleic acid sequence thus isolated.

According to the present invention there is provided a method of detecting at least one nucleic acid intended to be detected in a sample which comprises the steps of:

(1a) providing a sample for which it is to be determined whether at least one nucleic acid intended to be detected is contained therein or not, the nucleic acid intended to be detected being referred to hereinbelow as nucleic acid (I);

(1b) providing a single stranded nucleic acid which is complementary to the nucleic acid (I) and has a length such that it is shorter than the nucleic acid (I) but is long enough for hybridizing specifically with the nucleic acid (I), the single stranded nucleic acid being referred to hereinbelow as nucleic acid (II);

(1c) causing, in the sample, the nucleic acid (I) in the form of a single strand which is the nucleic acid (I) itself when the nucleic acid (I) is of a single stranded structure or which is at least one of the two strands of the nucleic acid (I) when the nucleic acid (I) is of a double stranded structure to hybridize with the nucleic acid (II), and subjecting the hybridization product to a chain-extending reaction wherein unit nucleic acids are added to the nucleic acid (II) which functions as a primer for the chain-extending reaction so as to extend the length of the nucleic acid (II) thereover thereby to produce a nucleic acid which is complementary to the nucleic acid (I), the nucleic acid thus produced and comprising the nucleic acid (II) as a primer being herein referred to as a synthesized nucleic acid, whereby a nucleic acid of a double stranded structure is produced;

(1d) optionally, practicing the steps (1b) and (1c) for each of the strands of the nucleic acid (I) when the nucleic acid (I) is of a double stranded structure to produce nucleic acids of a double stranded structure, disintegrating the double stranded structures into each of the strands, and causing, in the sample, the strands of the synthesized nucleic acids thus freed to hybridize with each other due to their inherent complementarity;

(1e) optionally, disintegrating the double stranded structure of a nucleic acid or nucleic acids eventually obtained from the steps (1a) to (1c) or (1a) to (1d) into each of the strands, causing at least one of each of the strands to hybridize with a nucleic acid (II) and subjecting the hybridization product to a chain-extending reaction to produce a double stranded structure in which one of the strands comprises a synthesized nucleic acid or subjecting each of the strands of the nucleic acid (I) when the nucleic acid (I) is of a double stranded structure to a chain-extending reaction to produce nucleic acids of a double stranded structure in which one of the strands comprises a synthesized nucleic acid; disintegrating the double stranded structure into each of the strands, and causing, in the sample, the thus freed strands of the synthesized nucleic acids to hybridize with each other due to their inherent complementarity so as to produce a double stranded structure;

(1f) optionally, practicing the step (1e), causing at least one of the strands of the nucleic acid of a double stranded structure eventually obtained from the practice of step (1e), said one of the strands having been freed from the double stranded structure, to hybridize with the nucleic acid (II); subjecting the hybridization product to a chain-extending reaction whereby a double stranded structure is produced as defined in the step (1c) and then optionally practicing at least once and successively steps of disintegration of the double stranded structure produced and the chain-extending reaction;

(1ff) optionally, when the nucleic acid (I) is of a double stranded structure and the step (1f) is practiced on both strands of the nucleic acid (I), disintegrating the double stranded structure into each of the strands, and causing, in the sample, the thus freed strands of the synthesized nucleic acids, each of which strands of the synthesized nucleic acid have been hybridized with each strand of the nucleic acid (I) of a double stranded structure, to hybridize with each other due to their inherent complementarity so as to produce a double stranded structure;

(1g) optionally, providing a single stranded nucleic acid, being referred to as nucleic acid (III), which is complementary to the upstream portion of the nucleic acid (I), which upstream portion of the nucleic acid (I) lies upstream in the direction to the 5'-end from the portion of the nucleic acid (I) which hybridizes with the nucleic acid (II), which nucleic acid (III) has a length such that it is shorter than the upstream portion of the nucleic acid (I) but is long enough for hybridizing specifically with the upstream portion of the nucleic acid (I);

(1h) optionally, practicing the steps (1a) to (1c), (1a) to (1d), (1a) to (1e), or (1f) or (1ff) to produce a double stranded nucleic acid, causing at least one of the strands of the double stand nucleic acid, said one of the strands having been freed from the double stranded structure, to hybridize with the nucleic acid (III); subjecting the hybridization product to a chain-extending reaction whereby a double stranded structure is produced or subjecting each of the strands of the nucleic acid (I) when the nucleic acid (I) is of a double stranded structure to a chain-extending reaction whereby a double stranded structure is produced one of the strands of the double stranded structure comprising a synthesized nucleic acid; disintegrating the double stranded structure into each of the strands; causing, in the sample, the thus freed strands of the synthesized nucleic acids to hybridize with each other due to their inherent complementarity so as to produce a double stranded structure;

(1i) optionally, practicing the step (1h) causing at least one of the strands of the nucleic acid of a double stranded structure eventually obtained from the practice of step (1h), said one of the strands having been freed from the double stranded structure, to hybridize with the nucleic acid (III) and/or the nucleic acid (II); subjecting the hybridization product to a chain-extending reaction whereby a double stranded structure is produced and then optionally practicing at least once and successively steps of disintegration of the double stranded structure produced and the chain-extending reaction;

(1ii) optionally, when the nucleic acid (I) is of a double stranded structure and the step (1i) is practiced on both strands of the nucleic acid (I), disintegrating the double stranded structure into each of the strands, and causing, in the sample, the thus freed strands of the synthesized nucleic acids, each of which strands of the synthesized nucleic acid have been hybridized with each strand of the nucleic acid (I) of a double stranded structure, to hybridize with each other due to their inherent complementarity so as to produce a double stranded structure;

(1j) causing the nucleic acid strand comprising the synthesized nucleic acid strand which is the product of either one of the steps (1c), (1d), (1e), (1f), (1ff), (1h), (1i) and (1ii), to eventually have at least a functionality (A) which is a label for detection, and providing a solid separation means for separating the nucleic acid strand comprising the synthesized nucleic acid strand from other nucleic acids in the sample, in which solid separation means a solid separation aid is used;

(1k) contacting the sample which has undergone the step (1j) with solid separation aid to separate the nucleic acid strand comprising the synthesized nucleic acid strand from the other nucleic acids; and (1l) subjecting the nucleic acid strand comprising the synthesized nucleic acid strand obtained from the practice of the step (1k) to detection operation wherein the functionality (A) is utilized to determine that the material subjected to the detection operation is the nucleic acid strand comprising the synthesized nucleic acid whereby the nucleic acid (I) in the sample is detected as an equivalent to the nucleic acid strand comprising the synthesized nucleic acid; the steps (1c) through (1j) being practiced irrespectively of whether or not the nucleic acid (I) is present in the sample.

The solid separation means using a solid separation aid set forth in the step (1j) for making it possible to separate the synthesized nucleic acid strand or the nucleic acid strand comprising the synthesized nucleic acid strand from other nucleic acids includes, in one embodiment:

(1) that the solid separation aid is a solid carrier; and (2) that the nucleic acid strand is caused to have, in addition to the functionality (A), a functionality (B) which is a site by which the nucleic acid strand can be combined with the solid carrier.

In the embodiment as shown above of the solid separation means, an actual practice of causing the synthesized nucleic acid strand or the nucleic acid strand comprising the synthesized nucleic acid strand to have both the functionalities ((A) and (B), separating the nucleic acids thus having the functionalities and detecting the very nucleic acid comprises the steps of:

(1) causing the double stranded nucleic acid which is the product of the steps (1c), (1d), (1e), (1f) and (1h), and (1i) and (1ii) to have the functionality (B) comprising a site by which the nucleic acid strand can be combined with the solid carrier and the functionality (A) comprising a detectable lable by:

(i) using a primer having one of the functionalities or primers such that one has one of the functionalities and one has the other of the functionalities and using a unit nucleic acid having one of the functionalities or unit nucleic acids such that one has one of the functionalities and one has the other of the functionalities thereby to obtain the synthesized nucleic acid strand as one having the functionalities (A) and (B); or (ii) forming the synthesized nucleic acid strand as one having one of the functionalities and then introducing thereinto, in the sample, the other of the functionalities;

(2) causing the nucleic acid strand having the functionalities (A) and (B) as the product of the step (1) to be combined, in the sample, with the solid carrier by means of the functionality (B) which is a site by which the nucleic acid strand is combined with the carrier;

(3) rinsing the solid carrier obtained from the step (2) thereby to remove any nucleic acids which are not combined with the solid carrier; and (4) subjecting the solid carrier obtained from the step (3) to detecting operation wherein the functionality (A) comprising the label is utilized to determine that there is a nucleic acid combined with the solid carrier whereby the nucleic acid is detected as an equivalent to the nucleic acid to be detected.

In the method of detection wherein a solid carrier is used as a solid separation aid in accordance with the present invention, the following steps (1) through (5) may optionally be practiced:

(1) the double stranded nucleic acid formed in the step (1c) is optionally disintegrated in the sample whereby the synthesized nucleic acid strand is freed from the double stranded nucleic acid;

(2) the double stranded nucleic acid formed in the step (1e) is optionally disintegrated in the sample whereby the synthesized nucleic acid strand is freed from the double stranded nucleic acid;

(3) the double stranded nucleic acid formed in the step (1f) or (1ff) is optionally disintegrated in the sample whereby the synthesized nucleic acid strand is freed from the double stranded nucleic acid;

(4) the double stranded nucleic acid formed in the step (1h) is optionally disintegrated in the sample whereby the synthesized nucleic acid strand is freed from the double stranded nucleic acid;

(5) the double stranded nucleic acid formed in the step (1i) or (1ii) is optionally disintegrated in the sample whereby the synthesized nucleic acid strand is freed from the double stranded nucleic acid;

The detection method in accordance with the present invention in which such a solid carrier is used is such that at least one primer which is complementary to the nucleic acid to be detected is used, and a nucleic acid sequence which is a product of chain-extending reaction over the primer or a double stranded nucleic acid formed by the nucleic acids which are the product of the chain-extending reaction of the primer is immobilized on the solid carrier, and the nucleic acid thus immobilized is subjected to detection operation.

The solid separation means using a solid separation aid set forth in the step (1j) for separating the synthesized nucleic acid or the nucleic acid strand comprising the synthesized nucleic acid strand from the other nucleic acids includes, in another embodiment:

(1) that the solid separation aid is a solid adsorbent which is capable of adsorbing selectively either one of a double stranded nucleic acid or a single stranded nucleic acid and a unit nucleic acid, and (2) the nucleic acid strand is in a double stranded state.

In the embodiment as shown above of the solid separation means, an actual practice of causing the synthesized nucleic acid strand or the nucleic acid strand which is the synthesized nucleic acid to have the functionality (A) comprising a detectable label, separating the nculeic acid thus having the functionality and detecting the very nucleic acid strand comprises the steps of:

(1) causing the double stranded nucleic acid which is the product of either of the steps (1c), (1d), (1e), (1f), (1ff), (1h), (1i) and (1ii) to have the functionality (A) comprising a detectable label by:

(i) using a nucleic acid (II) or (III) which has the functionality (A);

(ii) when a nucleic acid (II) or (III) which does not have the functionality (A), forming the synthesized nucleic acid as one having the functionality (A) by the use of a unit nucleic acid having the functionality (A);

(iii) forming the synthesized nucleic acid as one which does not have the functionality (A), and then introducing thereinto, in the sample, the functionality (A).

(2) providing, as the solid separation aid, a solid adsorbent which is capable of selectively adsorbing either of a double stranded nucleic acid or a single stranded nucleic acid and a unit nucleic acid;

(3) contacting the sample containing the double stranded nucleic acid having the functionality (A) with the solid adsorbent thereby to separate the double stranded nucleic acid from the single stranded nucleic acid and/or the unit nucleic acid;

(4) subjecting the double stranded nucleic acid having the functionality (A) obtained from the step (3) to detecting operation wherein the functionality (A) comprising the label is utilized to determine that there is a nucleic acid whereby the nucleic acid is detected as an equivalent to the nucleic acid to be detected.

The detection method in accordance with the present invention in which a solid adsorbent is used as the solid separation aid is such that at least one primer is used, and a double stranded nucleic acid which is a product of chain-extending reaction over the primer or is a double stranded nucleic acid formed by the nucleic acids which are the product of the chain-extending reaction of the primer, is separated from single stranded nucleic acids or a unit nucleic acids, and the nucleic acid thus separated is subjected to detection operation.

According to the present invention in the first embodiment, there is provided:

A method of detecting at least one nucleic acid intended to be detected in a sample which comprises the steps of:

(2a) providing a sample for which it is to be determined whether at least one nucleic acid intended to be detected is contained therein or not, the nucleic acid intended to be detected being referred to hereinbelow as nucleic acid (I);

(2b) providing a single stranded nucleic acid which is complementary to the nucleic acid (I) and has a length such that it is shorter than the nucleic acid (I) but is long enough for hybridizing specifically with the nucleic acid (I), the single stranded nucleic acid being referred to hereinbelow as nucleic acid (II);

(2c) causing, in the sample, the nucleic acid (I) in the form of a single strand which is the nucleic acid (I) itself when the nucleic acid (I) is of a single stranded structure or which is at least one of the two strands of the nucleic acid (I) when the nucleic acid (I) is of a double stranded structure to hybridize with the nucleic acid (II), and subjecting the hybridization product to a chain-extending reaction wherein unit nucleic acids are added to the nucleic acid (II) which functions as a primer for the chain-extending reaction so as to extend the length of the nucleic acid (II) thereover thereby to produce a nucleic acid which is complementary to the nucleic acid (I), the nucleic acid thus produced and comprising the nucleic acid (II) as a primer being herein referred to as a synthesized nucleic acid, whereby a nucleic acid of a double stranded structure is produced;

(2d) optionally, disintegrating in the sample the nucleic acid of a double stranded structure so as to free therefrom the synthesized nucleic acid strand;

(2e) optionally, practicing the steps (2b), (2c) and (2d) for each of the strands of the nucleic acid (I) when the nucleic acid (I) is of a double stranded structure to produce nucleic acids of a double stranded structure, disintegrating the double stranded structures into each of the strands, and causing, in the sample, the strands of the synthesized nucleic acids thus freed to hybridize with each other due to their inherent complementarity;

(2f) optionally, disintegrating the double stranded structure of a nucleic acid or nucleic acids eventually obtained from the steps (2a) to (2c) or (2a) to (2e) into each of the strands, causing at least one of each of the strands to hybridize with a nucleic acid (II) and subjecting the hybridization product to a chain-extending reaction to produce a double stranded structure in which one of the strands comprises a synthesized nucleic acid, or subjecting each of the strands of the nucleic acid (I) when the nucleic acid (I) is of a double stranded structure to a chain-extending reaction to produce nucleic acids of a double stranded structure in which one of the strands comprises a synthesized nucleic acid; disintegrating the double stranded structure into each of the strands, and causing, in the sample, the thus freed strands of the synthesized nucleic acids to hybridize with each other due to their inherent complementarity so as to produce a double stranded structure;

(2g) optionally, disintegrating the nucleic acid of a double stranded structure obtained in the step (2f) so as to free the synthesized nucleic acid strand;

(2h) optionally, practicing the step (2f), causing at least one of the strands of the nucleic acid of a double stranded structure eventually obtained from the practice of step (2f), said one of the strands having been freed from the double stranded structure, to hybridize with the nucleic acid (II); subjecting the hybridization product to a chain-extending reaction whereby a double stranded structure is produced and then optionally practicing at least once and successively steps of disintegration of the double stranded structure produced and the chain-extending reaction;

(2hh) optionally, when the nucleic acid (I) is of a double stranded structure and the step (2h) is practiced on both strands of the nucleic acid (I), disintegrating the double stranded structure into each of the strands, and causing, in the sample, the thus freed strands of the synthesized nucleic acids, each of which strands of the synthesized nucleic acid have been hybridized with each strand of the nucleic acid (I) of a double stranded structure, to hybridize with each other due to their inherent complementarity so as to produce a double stranded structure;

(2i) optionally, disintegrating the nucleic acid of a double stranded structure obtained in the step (2hh) so as to free the synthesized nucleic acid strand;

(2j) causing the nucleic acid of a double stranded structure in the sample obtained from the step (2c), (2e), (2f), (2h) or (2hh) to eventually have both of the functionalities (A) and (B) by either of the steps:

(i) using the primer which has one of the functionalities or which is in two types having either one of the two types of functionalities, respectively, or the primer having no such functionalities, and using the unit nucleic acid which has one of the functionalities or which is in two types having either one of the two types of functionalities, respectively, or the unit nucleic acid having no such functionalities, whereby the synthesized nucleic acid strand which has both the functionalities is obtained; or (ii) producing the synthesized nucleic acid strand as one having either one of the two types of functionalities and then introducing into the synthesized nucleic acid strand thus produced, in the sample, the other types of functionalities;

(2k) causing, in the sample, the synthesized nucleic acid strand having both of the functionalities obtained from the step (2j) to be combined with the solid carrier through the functionality (B);

(2l) washing the solid carrier having the synthesized nucleic acid combined therewith obtained from the step (2k) thereby to remove any nucleic acids which are not combined with the solid carrier; and (2m) subjecting the solid carrier obtained from the step (2l) to detection operation wherein the functionality (A) is utilized to determine that there is a nucleic acid combined with the solid carrier and having the functionality (A) whereby the nucleic acid (I) in the sample is detected as an equivalent to the nucleic acid combined with the solid carrier, the steps (2c) through (2j) being practiced irrespectively of whether or not the nucleic acid (I) is present in the sample.

According to the present invention in the second embodiment, there is provided:

A method of detecting at least one nucleic acid intended to be detected in a sample which comprises the steps of:

(3a) providing a sample for which it is to be determined whether at least one nucleic acid intended to be detected is contained therein or not, the nucleic acid intended to be detected being referred to hereinbelow as nucleic acid (I);

(3b) providing a single stranded nucleic acid which is complementary to the nucleic acid (I) and has a length such that it is shorter than the nucleic acid (I) but is long enough for hybridizing specifically with the nucleic acid (I), the single stranded nucleic acid being referred to hereinbelow as nucleic acid (II);

(3c) causing, in the sample, the nucleic acid (I) in the form of a single stranded which is the nucleic acid (I) itself when the nucleic acid (I) is of a single stranded structure or which is at least one of the two strands of the nucleic acid (I) when the nucleic acid (I) is of a double stranded structure to hybridize with the nucleic acid (II), and subjecting the hybridization product to a chain-extending reaction wherein unit nucleic acids are added to the nucleic acid (II) which functions as a primer for the chain-extending reaction so as to extend the length of the nucleic acid (II) thereover thereby to produce a nucleic acid which is complementary to the nucleic acid (I), the nucleic acid thus produced and comprising the nucleic acid (II) as a primer being herein referred to as a synthesized nucleic acid, whereby a nucleic acid of a double stranded structure is produced;

(3d) optionally, practicing the steps (3b) and (3c) for each of the strands of the nucleic acid (I) when the nucleic acid (I) is of a double stranded structure to produce nucleic acids of a double stranded structure, disintegrating the double stranded structures into each of the strands, and causing, in the sample, the strands of the synthesized nucleic acids thus freed to hybridize with each other due to their inherent complementarity;

(3e) optionally, disintegrating the double stranded structure of a nucleic acid or nucleic acids eventually obtained from the steps (3a) to (3c) or (3a) to (3d) into each of the strands, causing at least one of each of the strands to hybridize with a nucleic acid (II) and subjecting the hybridization product to a chain-extending reaction to produce a double stranded structure in which one of the strands comprises a synthesized nucleic acid or subjecting each of the strands of the nucleic acid (I) when the nucleic acid (I) is of a double stranded structure to a chain-extending reaction to produce nucleic acids of a double stranded structure in which one of the strands comprises a synthesized nucleic acid; disintegrating the double stranded structure into each of the strands, and causing, in the sample, the thus freed strands of the synthesized nucleic acids to hybridize with each other due to their inherent complementarity so as to produce a double stranded structure;

(3f) optionally, practicing the step (3e), causing at least one of the strands of the nucleic acid of a double stranded structure eventually obtained from the practice of step (3e), said one of the strands having been freed from the double stranded structure, to hybridize with the nucleic acid (II); subjecting the hybridization product to a chain-extending reaction whereby a double stranded structure is produced and then optionally practicing at least once and successively steps of disintegration of the double stranded structure produced and the chain-extending reaction;

(3ff) optionally, when the nucleic acid (I) is of a double stranded structure and the step (3f) is practiced on both strands of the nucleic acid (I), disintegrating the double stranded structure into each of the strands, and causing, in the sample, the thus freed strands of the synthesized nucleic acids, each of which strands of the synthesized nucleic acid have been hybridized with each strand of the nucleic acid (I) of a double stranded structure, to hybridize with each other due to their inherent complementarity so as to produce a double stranded structure;

(3g) optionally, providing a single stranded nucleic acid, being referred to as nucleic acid (III), which is complementary to the upstream portion of the nucleic acid (I), which upstream portion of the nucleic acid (I) lies upstream in the direction to the 5'-end from the portion of the nucleic acid (I) which hybridizes with the nucleic acid (II), which nucleic acid (III) has a length such that it is shorter than the upstream portion of the nucleic acid (I) but is long enough for hybridizing specifically with the upstream portion of the nucleic acid (I);

(3h) optionally, practicing the steps (a) to (3c), (3a) to (3d), (3a) to (3e), or (3f) or (10ff), causing at least one of the strands of the nucleic acid obtained from the practice of steps (3a) to (3c), (3a) to (3d), (3a) to (3e), or (3f) or (3ff), said one of the strands having been freed from the double stranded structure, to hybridize with the nucleic acid (III); subjecting the hybridization product to a chain-extending reaction whereby a double stranded structure is produced, or subjecting each of the strands of the nucleic acid (I) when the nucleic acid (I) is of a double stranded structure to a chain-extending reaction whereby a double stranded structure is produced, one of the strands of the double stranded structure comprising a synthesized nucleic acid; disintegrating the double stranded structure into each of the strands; causing, in the sample, the thus freed strands of the synthesized nucleic acids to hybridize with each other due to their inherent complementarity so as to produce a double stranded structure;

(3i) optionally, practicing the step (3h) causing at least one of the strands of the nucleic acid of a double stranded structure eventually obtained from the practice of step (3h), said one of the strands having been freed from the double stranded structure, to hybridize with the nucleic acid (III) and/or the nucleic acid (II); subjecting the hybridization product to a chain-extending reaction whereby a double stranded structure is produced and then optionally practicing at least once and successively steps of disintegration of the double stranded structure produced and the chain-extending reaction;

(3ii) optionally, when the nucleic acid (I) is of a double stranded structure and the step (3i) is practiced on both strands of the nucleic acid (I), disintegrating the double stranded structure into each of the strands, and causing, in the sample, the thus freed strands of the synthesized nucleic acids, each of which strands of the synthesized nucleic acid have been hybridized with each strand of the nucleic acid (I) of a double stranded structure, to hybridize with each other due to their inherent complementarity so as to produce a double stranded structure;

(3j) causing the nucleic acid of a double stranded structure in the sample obtained from the step (3c), (3d), (3e), (3f), (3ff), (3h), (3i) or (3ii) to eventually have the functionality (A) by either of the steps:

(ji) using the nucleic acid (II) or (III) having the functionality (A), (jii) using the unit nucleic acid having the functionality (A), when the nucleic acid (II) or (III) which does not have the functionality (A) is used, to form the synthesized nucleic acid as one having the functionality (A), or (jiii) producing the synthesized nucleic acid strand as one having no functionality (A) and then introducing into the synthesized nucleic acid thus produced, in the sample, the functionality (A);

(3k) causing the sample which contains the double stranded nucleic acid having the functionality (A) to contact with a solid adsorbent which selectively adsorbs either one of (i) a nucleic acid of a double stranded structure and (ii) a nucleic acid of a single stranded structure and or the unit nucleic acid thereby to effect the separation of the nucleic acid of a double stranded structure from the single stranded nucleic acid and/or the unit nucleic acid; and (3l) subjecting the nucleic acid of a double stranded structure having the functionality (A) obtained from the step (3k) to detection operation wherein the functionality (A) is utilized to determine that the material subjected to the detection operation is the nucleic acid of a double stranded structure whereby the nucleic acid (I) in the sample is detected as an equivalent to the nucleic acid of a double stranded structure, the steps (3c) through (3k) being practiced irrespectively of whether or not the nucleic acid (I) is present or not.

In the present invention, the specific feature resides in that presence of at least one objective nucleic acid in a sample can be detected simultaneously and yet rapidly.

The method for detecting a nucleic acid sequence according to the present invention, as defined above, comprises obtaining a synthesized nucleic acid strand which is the labelled duplicate in nucleic acid sequence or "a copy" of a detection object according to a series of the reactions by use of polymerase, etc., separating the labelled nucleic acid strand from other nucleic acids by use of a separation means using a solid phase separation means which enables separation of the synthesized nucleic acid strand or the nucleic acid strand containing the synthesized nucleic acid strand from other nucleic acids and detecting the label of the nucleic acid strand, thereby detecting the objective gene. More specifically, in the first embodiment, the method comprises obtaining a labelled nucleic acid strand (double-stranded or single-stranded nucleic acid) of a detection object endowed with two kinds of functionalities (A) and (B) and detecting the objective gene by means of one of the functional groups for fixing onto a solid phase carrier and the other as the functional group for detection. In the second embodiment, the method comprises obtaining a duplicate or "a copy" of a detection object labelled with a detectable functionalities group (labelled double-stranded nucleic acid), separating this with the use of an appropriate solid adsorbent from the single-stranded primer or labelled unit nucleic acid which may also be labelled in the test sample and detecting only the objective double-stranded nucleic acid adsorbed, thereby detecting the objective gene. Thus, no cumbersome operation of hybridization is required, and the device utilized at present in other fields such as in the field of antigen-antibody reaction can be readily applied to the present method. As the result, a large number of test samples can be analyzed at one time.

In addition, since no hybridization of nucleic acid nor separation of nucleic acid by gel electrophoresis is required, the sample containing nucleic acid to be detected can be under the crude purified state, and preparation of the sample can be done easily by use of a device.

Also, since the chain-extending reaction with a primer is carried out without performing hybridization, the analysis time can be shortened to a great extent. Further, the labelling material which is to be prepared previously in the present detection method are labelled primer or labelled mononucleotide as the unit nucleic acid which can be chemically synthesized in large amounts, and therefore it is not necessary to label natural DNA fragments with the use of an enzyme, etc. as in the hybridization method of the prior art.

Further, in the respective samples to be detected, even when the base sequence of the objective nucleic acid (I) may differ delicately (by one or more bases), the case where the primer is completely complementary to the objective nucleic acid and the case where it is not can be distinguished from each other by controlling appropriately the reaction conditions such as a type and/or quantity of a polymerase used, etc. In short, even the point mutation can be easily detected without recourse to the hybridization method, etc.

By use of plural types of primers labelled with labels with different functional groups, the chain-extending reactions can be peformed for one or more kinds of nucleic acids (I) at the same time, and by performing the detection operations utilizing the functional groups of the respective labels, presence of a large number of objective nucleic acids can be determined at the same time.

BEST MODE FOR PRACTICING THE INVENTION

Figure 1A:
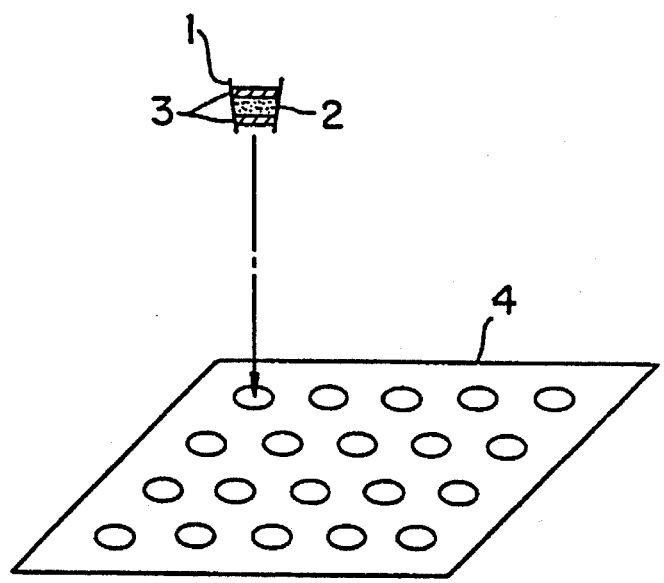
FIGS. 1A, 1B and 1C are illustrations showing the microplate filled with a solid adsorbent which can correspond to the automatic instrument for microplate.
Figure 1B:
Figure 1B:
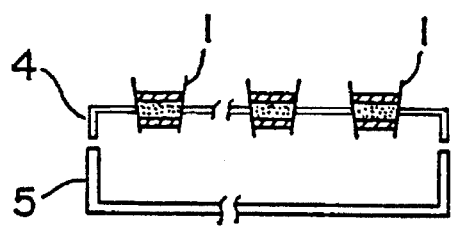
Figure 1C:
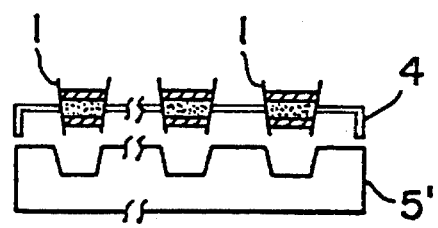

The method for detecting at least one objective nucleic acid according to the present invention comprises the steps (1a) to (1l) as specified above, and detects the objective gene by obtaining a synthesized nucleic acid strand which is the labelled duplicate (nucleic acid sequence) of a detection object according to a series of the reactions by use of polymerase, etc., separating said labelled nucleic acid strand from other nucleic acids by use of a separation means using a solid phase separation aid which enables separation of the synthesized nucleic acid strand or the nucleic acid strand containing the synthesized nucleic acid strand from other nucleic acids and detecting the label of the nucleic acid strand.

The specific embodiments of the detection method according to the present invention include the first embodiment, wherein the separation means using a solid separation aid basically includes that:

(1) the solid phase separation aid is a solid phase carrier; and (2) the nucleic acid strand is endowed with a functionality (B) comprising a site which can be bound to the solid phase carrier in addition to the functionality (A), and the second embodiment wherein the above separation means using a solid separation aid includes that:

(1) the solid separation aid is a solid adsorbent having selective adsorbability for either one of (i) double-stranded nucleic acid and (ii) single-stranded nucleic acid and unit nucleic acids; and (2) the nucleic acid strand is under the double-stranded state.

FIRST EMBODIMENT

Detection Principle

The first embodiment in the method for detecting at least one objective nucleic acid according to the present invention comprises the above steps (2a) to (2m) and this method is based in principle on that (i) from an objective nucleic acid in a test sample (called nucleic acid (I)), a nucleic acid complementary thereto (this nucleic acid is called synthesized nucleic acid) is made in the test sample and detection thereof is conducted, (ii) the synthesized nucleic acid in the test sample is immobilized on a solid carrier and detected by utilizing the label on the synthesized nucleic acid, and (iii) for performing the above (ii), the synthesized nucleic acid is obtained as having a functionality comprising a binding site to the solid carrier and a functionality comprising a label introduced therein, and introduction of the functionality is effected so that only the synthesized nucleic acid may have both the functionalities but co-existing nucleic acids will not have both of the functional groups (the above step (2j)), thereby making detection on the solid carrier selective.

Thus, the synthesized nucleic acid having transcribed the base sequence of the objective nucleic acid is such that only it is endowed with both the above functionalities in the test sample, that is, the co-existing non-objective nucleic acids have no functional group of these or only one of them (for example, the binding site onto the solid carrier), and, accordingly, when the test sample is contacted with the solid carrier and the solid carrier is then washed, the co-existing nucleic acids having no binding site onto the carrier will be washed away and on the other hand the co-existing nucleic acids having such site with no label may be bound to the solid but will not be detected due to the lack of the label, and therefore when the detection operation is practiced of the solid carrier on which the nucleic acids are bound, only the synthesized nucleic acid having both the functionalities which is equivalent to the objective nucleic acid is detected, thus enabling the above selective detection. If there exists no objective nucleic acid, no synthesized nucleic acid will be formed, and since there is also no labelled nucleic acid bound to the solid carrier, the detection result reveals absence of the objective nucleic acid in the test sample.

Introduction of both the above functionalities to realize such selective detectability should be preferably performed by such a method that, when a so-called primer (the above nucleic acid (II)) is used and a chain-extending reaction is conducted by extending a strand length of and from the primer with DNA polymerase if the objective nucleic acid is DNA and after the DNA has been disintegrated into a single strand, or with a reverse transcriptase if the objective nucleic acid is RNA, use is made of a primer having none, either one or individually both (namely two kinds or more of a primer) of both functionalities and use is made of a monomer or unit nucleic acid for the strand length elongation having none, either one or individually both (namely two kinds or more of a unit nucleic acid) of both functional groups, to obtain said synthesized nucleic acid strand as one having both functional groups. Specific examples of the synthesized nucleic acid strand having both the functionalities thus obtained may include (i) one obtained by hybridizing a primer having a binding site onto a solid carrier (nucleic acid (II)) to one of the strand when the objective nucleic acid (I) is a double-stranded DNA, or when it is a single-stranded DNA, to that strand, and extending the strand length of said primer in the presence of at least one of dATP, dTTP, dGTP, dCTP, etc. (described in detail hereinafter) as the unit nucleic acids under the action of DNA polymerase, wherein one or one kind or plural number or plural kinds of the unit nucleic acid having a label are used, to form a double-stranded strand consisting of the original DNA strand and the synthesized nucleic acid strand; (ii) one obtained by forming a double-stranded structure as described above for one of the double-stranded DNA strand (with proviso that no unit nucleic acid having a label is used), forming also a double-stranded structure as described above for the other DNA strand (with proviso that a primer having a label is used), liberating the synthesized strands by removing the strands derived from the original DNA from both double-stranded structures, effecting hybridization of the both synthesized strands to form a double-stranded structure having both functionalities supplied from the primer (for each synthesized strand liberated, addition of the primer and/or extension of the strand length or formation of synthesized strand can be also effected to amplify the double-stranded structure comprising the synthesized strand); and others.

Introduction of both functionalities can be also practiced according to other methods suited for the purpose. For example, there can be employed a method in which a synthesized strand is formed with one of the functionalities imparted to the primer and/or the unit nucleic acid, and thereafter the other functionalities are introduced.

The labelled synthesized nucleic acid also has a binding site on to a solid carrier, and in this case "the binding site on to a solid carrier" is not required to be a site capable of binding directly to the solid carrier. In other words, it may be also one which can realize binding with the solid carrier through a substance capable of promoting binding between both said site on the synthesized nucleic acid side and the binding site on the solid carrier side by existing between both ("reagent for trapping" (described in detail hereinafter)). The reagent for trapping may be either previously bound to the binding site on the synthesized nucleic acid side or to said binding site on the solid carrier side.

Also, the chain-extending reaction of the primer with polymerase can be carried out with the use of respectively separate primers having separate functional groups (labels) to detect simultaneously a plural number of nucleic acids (I) in the same test sample.

Practice of Detection a. Nucleic Acid

The nucleic acid to be detected as herein mentioned have the base sequence to be detected, and may be either RNA or DNA. Such nucleic acids can be prepared from all living bodies such as *E. coli*, viruses and higher animals and vegetables. Also, when the above nucleic acid is used for the present detection method, the nucleic acid may be either purified or not.

b. Primer and its Chain-Extending Reaction (i) Primer (nucleic acid (II))

The primer as herein mentioned forms specifically a complementary strand with the above nucleic acid to be detected (in the case of DNA, the double-stranded nucleic acid sequence is required to be disintegrated into a single-stranded strand by such means as denaturation, etc.), having its 3'-end to which mononucleotides are successively added, and requires indispensably the hydroxyl group at the 3'-end. In general, primer refers to an oligodeoxyribonucleotide, but it can be also a longer strand DNA fragment obtained from nature. It should have a length enough to hybridize specifically with the objective nucleic acid (nucleic acid (I)).

When the point mutation is to be detected, two kinds of primers are used; a primer which has a length enough to hybridize with the objective nucleic acid that has undergone the point mutuation and is completely complementary thereto and a primer which has a length enough to hybridize with said nucleic acid that has not undergone the point mutation and is completely complementary thereto. These primers are both oligodeoxyribonucleotides.

As specific examples of such primers, there can be used, for example:

(a) a primer without any modification at all;

(b) primers having a site bindable to a solid phase carrier;

(c) primers into which a label has been introduced;

(d) primers different from each other, one of which has a site bindable to a solid phase carrier and the other has a label introduced therein; etc.

The label or the site bindable to a solid phase carrier of the primer as herein mentioned may be located at any position on the primer which does not interfere with chain-extending reaction of the primer, but preferably at the 5'-end.

As the label, either non-radioactive or radioactive may be used.

Examples of the non-radioactive labels may include, other than biotin shown below in the experimental examples, 2,4-dinitrophenyl group, fluorescein and derivatives thereof [fluorescein isothiocyanate (FITC)], rhodamine and derivatives thereof [e.g. tetramethylrhodamine isothiocyanate (TRITC), Texas Red, etc.], 4-fluoro-7-nitrobenzofuran (NBDF) and fluorescent substances such as Dansyl or chemiluminescent substances, all of which can be used in labeling according to known means (see Japanese Patent Laid-Open Publications Nos. 93098/1984, 93099/1984) which respectively correspond to U.S. Pat. Nos. 4,667,025 and 4,789,737 (Miyoshi et al.).

When to be labelled with a radioactive substance, the labelling substance can be introduced by known means by use of, for example, a radioisotope such as $^{131}I$, $^{133}I$, $^{14}C$, $^{3}H$, $^{35}S$, $^{32}P$, etc.

On the other hand, the site bindable to a solid phase carrier may be any one which can react selectively with said carrier. As an example, the above non-radioactive labelling substance can be used as such, and in that case, it must not be the same as the labelling substance to be used for detection. As a preferable specific example, biotin, or a fluorescent material such as fluorescein, etc., or a hapten such as 2,4-dinitrophenyl group, etc. can be previously introduced into the primer. The solid phase carrier as herein mentioned is as defined below.

Labelling of the primer with these may be practiced chemically, in the case when the primer is an oligodeoxyribonucleotide, after or simultaneously with chemical synthesis of the oligodeoxyribonucleotide (Japanese Patent Laid-Open Publication Nos. 93098/1984, 93099/1984).

Also, when the primer is a natural fragment, it can be chemically labelled [L. E. Orgel et al, Nucleic Acids Res. 14, 5591–5603, (1986)].

ii) Chain-extending reaction of primer

Of the above primers, the chain-extending reaction by use of the primer (d) (primers different from each other with one having a site bindable to a solid phase carrier and the other having a label introduced therein) for example, can be carried out by causing at least one of deoxyadenosine triphosphate, deoxyguanosine triphosphate, deoxycytidine triphosphate and thymidine triphosphate which are 4 kinds of deoxyribonucleotide triphosphates to be incorporated as the substrate in the primer. For this chain-extending reaction, E. coli DNA polymerase I, Klenow fragment of E. coli DNA polymerase, T4 DNA polymerase or a reverse transcriptase can be used. Particularly, by use of a heat-resistant enzyme which performs chain-extending reaction at a high temperature, specificity of target sequence recognition with the primer can be enhanced [F. F. Chehab et al: Nature 329, 293–294 (1987)].

Also, the reaction with use of the primer (c) (one in which only a label has been introduced) may be carried out in the presence of at least one deoxyribonucleotide triphosphate of the four kinds of deoxyribonucleotide triphosphates in which a site bindable to a solid phase carrier is introduced, the chain-extending reaction with use of the primer (b) (one in which only a site bindable to a solid phase carrier has been introduced) can be carried out in the presence of at least one deoxyribonucleotide triphosphate of the four kinds of deoxyribonucleotide triphosphates in which a label has been introduced, and the chain-extending reaction with use of the primer (a) (without any modification at all) can be carried out in the presence of at least one deoxyribonucleotide triphosphate of the four kinds of deoxyribonucleotide phosphates in which a site bindable to a solid phase carrier has been introduced, in the same manner as that of the primer (d) to generate a new labelled product in the course of the chain-extending reaction.

The four kinds of deoxyribonucleotide triphosphates having a label or a site bindable to a solid carrier introduced therein as herein mentioned are those in which a label or a site bindable to a solid phase carrier as defined above has been introduced into the base moiety of said nucleotide (with no modification added, and these compounds include various derivatives. Generally speaking, these respective derivatives may be sometimes reduced in efficiency to be incorporated into the primer, but can be incorporated similarly as the non-modified ones. However, a deoxyribonucleotide triphosphate labelled with a radioactive substance such as $^{32}P$ is incorporated at an efficiency to the same extent as the non-labelled one. Representative of non-radioactive labelled mononucleotide triphosphates is biotinylated mononucleotide triphosphate [P. R. Langer et al: Proc. Natl. Acad. Sci. USA 78, 6633–6637 (1981)], or otherwise those labelled with a fluorescent substance or a luminescent substance, or those bindable to antibody such as 2,4-dinitrophenyl group, may be used. The labelled mononucleotide phosphate derivatives differ from one another in efficiency to be incorporated in the chain-extending reaction, and also affinity with the enzyme to be used in the chain-extending reaction is important, and the combination of the derivative with the enzyme to be used in the chain-extending reaction must be sufficiently taken into consideration.

Also, when detection of higher sensitivity is required, particularly when the amount of the base sequence to be detected is small, the method for amplifying the base sequence can be used [Japanese Patent Laid-Open Publication No. 281/1987] which corresponds to U.S. Pat. Nos. 4,683,195; 4,683,202; and 4,800,159 (Mullis et al.). Thus, by use of the labelled primer and the labelled mononucleotide triphosphate as described above, the target base sequence endowed with two kinds of functionalities (a site bindable to a solid phase carrier or a label to be used for detection) can be obtained easily with amplification.

Also, for the chain-extending reaction of the primer to be initiated correctly at the desired position, such factors as the extent of complementarity between the primer and the template (namely the objective nucleic acid (I)), the length of the primer, the reaction temperature, etc. must be considered. Generally speaking, when the length of the primer is short or the extent of complementarity is low, the reaction must be carried out at a lower temperature, as a matter of course.

Also, for the chain-extending reaction of the primer to be carried out at a more correct position, it is possible that the double-stranded nucleic acid obtained after the first chain-extending reaction of the primer (nucleic acid (II)) is disintegrated into a single strand, and the single-stranded nucleic acid thus formed is subjected to another chain-extending reaction with the use of a single-stranded nucleic acid (nucleic acid (III)) which is complementary to the nucleotide portion of the objective nucleic acid (I) on its 5'-side relative to the nucleotide portion hybridized with the nucleic acid (II) and having a length shorter than but long enough to be specifically hybridized with said portion.

Further, when the point mutation, etc. is to be detected by use of the present method, the chain-extending conditions of the primer must be considered to greater extent than that as described above. For example, in order to make a difference in stability between one and another double stranded formed between the primer and the objective nucleic acid (I) (the case when completely complementary and the case when not so), it is necessary to carry out the reaction with addition of DMSO in the reaction mixture or addition of a competitive primer (When the point mutation in the objective nucleic acid (I) is examined, the chain-extending reaction of the primer is carried out wherein use is made of a primer completely complementary to the normal nucleotide sequence and a primer completely complementary to the nucleotide sequence which has undergone the point mutation. At this time, if the base sequence in the objective nucleic acid (I) is normal, the latter primer is the competitive primer, while on the contrary when the point mutation has occurred in the nucleotide sequence in the objective nucleic acid (I), the former is the competitive primer.).

c. Solid Phase Carrier

The solid carrier as herein mentioned may be any material which is inert to the solvent and all the reagents used in the reaction and can be separated from said solution according to any kind of method. As such materials, for example, microtiter well, polystyrene balls, Agarose beads, polyacrylic beads, etc. can be used.

The above solid carrier, can be modified by previously introducing a reagent for trapping the double-stranded structure (one having a site bindable to the solid phase carrier and a label introduced therein) formed from the above primer chain-extending reaction thereby to effect fixation easily and selectively.

As such reagent for trapping, any reagent capable of reacting with the site in the above double-stranded structure bindable to the solid carrier may be used, preferably one capable of reaction under mild conditions. As the mode of binding between the reagent and the carrier, it may be either of covalent or of non-covalent bonding, provided that a specific bonding can occur. Preferably, the binding method which can retain the activity of the reagent for trapping to the maximum degree may be employed. As a specific example of these reagents for trapping, streptavidin, antibody, etc. may be employed.

For example, for trapping a biotin-labelled duplicate, a carrier having streptavidin bound thereto, and for a labelled product of fluorescein or 2,4-dinitrophenyl group, carriers having the respective antibodies bound thereon can be used.

d. Detection Method

After the solid phase carrier prepared according to the method as described above and the nucleic acid endowed with both the functionalities prepared according to the steps (2a) to (2j) are bound together by mixing them, other nucleic acids other than the objective nucleotide sequence not bound to the carrier and other contents than nucleic acids the in the test sample are washed out with an appropriate solvent. The appropriate solvent mentioned here means that all the reagents such as nucleic acids and label must be maintained stably as a matter of course, and also that it cannot give such condition as to cleave the bonding between the solid phase carrier and the synthesized nucleic acid, the reagent for trapping and the synthesized nucleic acid, between or the label and the synthesized nucleic acid. Also, when both the functionalities in the nucleic acid sequence having the double stranded portion exist separately on each strand of the complementary strands, the condition should not be such that the complementary strands are dissociated.

The washing method differs depending on the properties of the carrier for fixing, and may be conducted according to the method generally used in the field of antigen-antibody reaction.

According to such washing operation, only the duplicate (synthesized nucleic acid) of the objective nucleic acid to be detected (nucleic acid (I)) can be selectively fixed on the carrier.

Next, the labeled product fixed on the carrier can be detected as fixed on the carrier or in a free form in the solution. For detection in the free form, for example, there is a method in which the bonding between the labeled product and the reagent for trapping is cleaved, or a method in which the bonding between the label and the synthesized nucleic acid is cleaved, etc. [Herman, T. M. et al, Anal. Biochemistry 156, 48–55 (1986)]. Also, when the two types of the functionalities are located respectively on separate strands of the complementary strands, the double strands can be disintegrated by thermal denaturation or other known methods to set free the strand containing the label for detection into the solution.

When an amplification reaction is carried out by use of primers labelled with two kinds of different label and when a site of a restriction enzyme exists in the amplified sequence, after fixing onto the carrier, the fragment containing the label for detection can be freed from the solid phase carrier by use of the restriction enzyme.

On the other hand, if there is no cleaving site of the restriction enzyme in the amplified sequence, the fragment containing the label for detection cannot be freed from the carrier for detection, and it is thus possible to examine whether a cleaving site of a specific restriction enzyme exists in the amplified sequence or not by use of this method.

Practical detection of the labeled product may be done by use of general methods depending on the label employed. For example, if the label is a radioisotope, its activity as such may be measured. On the other hand, for example, if the label is biotin, it can be reacted with a substrate by use of avidin- or streptavidin-enzyme conjugate to obtain a component detectable by colorimetric or fluorescent means. Also, when, for example, the label is fluorescence, its intensity can be measured as such by use of a fluorophotometer.

Now, in measurement of a practical sample in the method as described above, it is important to take into consideration the following points.

The first is the non-specific chain-extending reaction in chain-extending reactions of primer. This is the chain-extending reaction which has occurred through binding of the primer to a site other than the objective base sequence, and for prevention of such non-specific chain-extending reaction, as generally considered, the GC content or length of the primer must be sufficiently investigated for each detection object. In this connection, the non-specific chain-extending reaction can be sufficiently cancelled by making the reaction temperature higher and can be also ameliorated by use of a heat-resistance DNA polymerase (NEB).

The second is the undesired reaction of the unreacted label with the reagent for trapping fixed on the carrier thereby interfering with the desired reaction of the labelled duplicate (synthesized nucleic acid) to be detected with the reagent for trapping. For solving this problem, firstly, it may be considered to make the trapping capacity of the reagent for trapping fixed on the carrier greater. Secondly, there is removal of unreacted label out of the system, and this can be done by simple gel filtration method, etc. in which the difference in properties between the labelled primer or labelled unit nucleic acid (mononucleotide triphosphate) and the duplicate to be detected (synthesized nucleic acid) is utilized [Maniatis et al: Molecular Cloning p. 466 (1982)]. However, those methods cannot necessarily be said to be preferable methods in view of automation of the process. From such point, it is important to select the reaction conditions which will make the residual amount of unreacted label as small as possible. For example, when the chain-extending reaction is carried out by use of one type of primer in which a site bindable to the solid phase carrier has been introduced with the nucleic acid (mononucleotide triphosphate) having a label introduced therein as the substrate, and when said site of the primer is bound to the reagent for trapping in the solid phase and when the labelled portion of mononucleotide triphosphate is used for detection the amount of the primer should be at such a level as not exceeding the trapping ability of the carrier.

The same is true also when employing two kinds of labelled primers, and the primers are used in amounts not larger than necessary, even if the efficiency of the duplicate formation may be lowered to some extent. However, the reaction condition to make the residual amount of unreacted label smaller is not required when the trapping capacity of the carrier having introduced the reagent therein is sufficient.

SECOND EMBODIMENT

Detection Principle

The second embodiment in the method for detecting an objective nucleic acid according to the present invention comprises the steps (3a) to (3l), and this method is based in principle on that (i) from an objective nucleic acid in a test sample (called nucleic acid (I)) is prepared a nucleic acid complementary thereto in the test sample (this nucleic acid is called synthesized nucleic acid) to form a double stranded structure, and detection is made thereof, that (ii) in preparation of the synthesized nucleic acid in the test sample, the unit nucleic acid for strand length elongation is labeled with a label substance having an appropriate functional group, namely introduction of the functionality (A), whereby the synthesized nucleic acid is obtained as having the label, or a label is introduced afterwards, and that (iii) the synthesized nucleic acid having a label introduced therein obtained in the above (ii) is separated from a single-stranded primer or the unit nucleic acid, and the objective labelled synthesized nucleic acid as an equivalent to the nucleic acid (I) is selectively detected.

Thus, when the chain-extending reaction with polymerase is carried out by use of a primer or unit nucleic acid labelled with an appropriate functional group, the label in the reaction mixture exists only in the synthesized nucleic acid and in the primer or the unit nucleic acid (the synthesized nucleic acid forms a double strand with the objective nucleic acid or forms a double strand mutually between the synthesized nucleic acids). Accordingly, when said synthesized nucleic acid is separated from the primer, a solid adsorbent which can separate the double-stranded nucleic acid from the single-stranded nucleic acid may be used, and when the synthesized nucleic acid is separated from the unit nucleic acid, a solid adsorbent which can separate the double-stranded nucleic acid from the unit nucleic acid may be used.

Thus, by detecting the synthesized nucleic acid having transcribed the nucleotide sequence of the objective nucleic acid with the use of the label introduced therein, the objective nucleic acid can be detected. If there is no objective nucleic acid present in the test sample, no synthesized nucleic acid having the label introduced therein exists, and the detection result is that the objective nucleic is absent in the test sample.

Introduction of the above functionalities to realize such selective detectability can be performed by use of a so called primer (the above nucleic acid (II)) and by extending the strand length from the primer with DNA polymerase, when the objective nucleic acid is DNA, after disintegrating the DNA into a single strand or with a reverse transcriptase when the objective nucleic acid is RNA, in which operation a primer having the functionality (A) or no such functionality is used, and a monomer or unit nucleic acid having the functionality or no such functionality is used, thereby obtaining said synthesized nucleic acid finally as one having the functionality (A). Specific examples of the synthesized nucleic acid strand having the functionality (A) thus obtained may include (i) one obtained by hybridizing a primer having a binding site onto a solid carrier (nucleic acid (II)) to one of the strand when the objective nucleic acid (I) is a double-stranded DNA, or when it is a single-stranded DNA, to that strand, and extending the strand length of said primer in the presence of at least one of dATP, dTTP, dGTP, dCTP, etc. (described in detail hereinafter) as the unit nucleic acids under the action of DNA polymerase, wherein one or one kind or plural number or plural kinds of the unit nucleic acid having a label are used, to form a double-stranded strand consisting of the original DNA strand and the synthesized nucleic acid strand; (ii) one obtained by forming a double-stranded structure as described above for one of the double-stranded DNA strand (with proviso that no unit nucleic acid having a label is used), forming also a double-stranded structure as described above for the other DNA strand (with proviso that a primer having a label is used), liberating the synthesized strands by removing the strands derived from the original DNA from both double-stranded structures, effecting hybridization of the both synthesized strands to form a double-stranded structure having both functionalities supplied from the primer (for each synthesized structure liberated, addition of the primer and/or extension of the strand length or formation of synthesized strand can be also effected to amplify the double-stranded structure comprising the synthesized strand); and others. Introduction of the functionality (A) can be practiced according to other methods suited for the purpose, and it is also possible to introduce any desired functionality after formation of the objective synthesized nucleic acid. In such reaction, the functionality to be introduced may be at least one kind.

Also, the chain-extending reaction of primer with polymerase can be conducted with the use of separate primers having different functionalities (A, A'. . . ) or the same functionality, whereby a plural number of objective nucleic acids in the same test sample can be simultaneously detected.

Practice of Detection a. Nucleic acid

The nucleic acid to be detected as herein mentioned have the base sequence to be detected, and may be either RNA or DNA. Such nucleic acids can be prepared from all living bodies such as *E. coli*, viruses and higher animals and vegetables. Also, when the above nucleic acid is used for the present detection method, the nucleic acid may be either purified or not.

b. Primer and its chain-extending reaction (i) Primer (nucleic acid (II))

The primer as herein mentioned forms specifically a complementary strand with the above nucleic acid to be detected (in the case of DNA, the double-stranded nucleic acid sequence is required to be disintegrated into a single-stranded strand by such means as denaturation, etc.), having its 3'-end to which mononucleotides are successively added, and requires indispensably the hydroxyl group at the 3'-end. In general, primer refers to an oligodeoxyribonucleotide, but it can be also a longer strand DNA fragment obtained from nature. It should have a length enough to hybridize specifically with the objective nucleic acid (nucleic acid (I)).

When the point mutation is to be detected, two kinds of primers are used; a primer which has a length enough to hybridize with the objective nucleic acid that has undergone the point mutuation and is completely complementary thereto and a primer which has a length enough to hybridize with said nucleic acid that has not undergone the point mutation and is completely complementary thereto. These primers are both oligodeoxyribonucleotides.

As specific examples of such a series of primers, a primer without any modification at all or a primer having a label introduced therein can be used.

The label for the primer as herein mentioned may be located at any position which does not interfere with chain-extending reaction of the primer, but preferably at the 5'-end.

As the label, either non-radioactive or radioactive may be used.

Examples of the non-radioactive substance may include fluorescein and derivatives thereof shown below in the experimental examples [fluorescein isothiocyanate (FITC)], rhodamine and derivatives thereof [e.g. tetramethyl-rhodamine isothiocyanate (TRITC), Texas Red, etc.], 4-fluoro-7-nitrobenzofuran (NBDF) and fluorescent substances such as Dansyl or chemiluminescent substances, all of which can be labelled according to known means (see Japanese Laid-Open Patent Publications Nos. 93098/1984, 93099/1984 which respectively correspond to U.S. Pat. Nos. 4,667,025 and 4,789,737 (Miyoshi et al.)).

When labelled with a radioactive substance, the label can be introduced by known means by use of, for example, a radioisotope element such as $^{131}$I, $^{133}$I, $^{14}$C, $^{3}$H, $^{35}$S, $^{32}$P, etc.

(ii) Chain-extending reaction of primer

Of the above primers, when a primer not labelled is used, the chain-extending reaction can be carried out by having at least one of deoxyadenosine triphosphate, deoxyguanosine triphosphate, deoxycytidine triphosphate and thymidine triphosphate which are 4 kinds of dexoyribonucleotide triphosphates incorporated as the substrate in the primer. Also, when a labelled primer is used, it is possible to have at least one of the above 4 kinds of labelled or non-labelled deoxyribonucleotide triphosphates similarly incorporated as the substrate in the primer. For this chain-extending reaction, *E. coli* DNA polymerase I, Klenow fragment of *E. coli* DNA polymerase, T4 DNA polymerase or a reverse transcriptase can be used. Particularly, by use of a heat-resistant enzyme which can perform chain-extending reaction at a high temperature, specificity of target sequence recognition with the primer can be enhanced and also in the case of detecting the point mutation, etc., this heat-resistant enzyme is preferred.

Also, when detection of higher sensitivity is required, particularly when the amount of the nucleotide sequence to be detected is small, the method for amplifying the nucleotide sequence can be used [Japanese Laid-Open Patent Publication No. 281/1987] which corresponds to U.S. Pat. Nos. 4,683,195; 4,683,202; and 4,800,159 to Mullis et al. That is, by use of the labelled primer and the labelled mononucleotide triphosphate as described above, the target nucleotide sequence endowed with two kinds of functionalities (a site bindable to solid phase carrier or a label to be used for detection) can be obtained easily with amplification.

Also, by carrying out the step successively stepwise the step of making the double-stranded nucleic acid obtained by the above chain-extending reaction of primer a single strand and again performing the chain-extention reaction with the primer, the synthesized nucleic acid strand labelled can be amplified to enhance the detection sensitivity.

Also, for the chain-extending reaction of the primer to be initiated correctly at the desired position, such factors as the extent of complementarity between the primer and the template (namely the objective nucleic acid (I)), the length of the primer, the reaction temperature, etc. must be considered. Generally speaking, when the length of the primer is short or the extent of complementarity is low, the reaction must be carried out at lower temperature, as a matter of course.

Also, for the chain-extending reaction of the primer to be carried out at a more correct position, it is possible that the double-stranded nucleic acid obtained after the first chain-extending reaction of the primer (nucleic acid (II)) is disintegrated into a single strand, and the single-stranded nucleic acid thus formed is subjected to another chain-extending reaction with the use of a single-stranded nucleic acid (nucleic acid (III)) which is complementary to the nucleotide portion of the objective nucleic acid (I) on its 5'-side relative to the nucleotide portion hybridized with the nucleic acid (II) and having a length shorter than but long enough to be specifically hybridized with said portion.

Further, when the point mutation, etc. is to be detected by use of the present method, the chain-extending conditions of the primer must be considered to greater extent than that as described above. For example, in order to make a difference in stability between one and another double stranded structures formed between the primer and the objective nucleic acid (I) (the case when completely complementary and the case when not so), it is necessary to carry out the reaction with addition of DMSO in the reaction mixture or addition of a competitive primer (When the point mutation in the objective nucleic acid (I) is examined, the chain-extending reaction of the primer is carried out wherein use is made of a primer completely complementary to the normal nucleotide sequence and a primer completely complementary to the nucleotide sequence which has undergone the point mutation. At this time, if the base sequence in the objective nucleic acid (I) is normal, the latter primer is the competitive primer, while on the contrary when the point mutation has occurred in the nucleotide sequence in the objective nucleic acid (I), the former is the competitive primer.).

c. Solid Adsorbent

The solid adsorbent as herein mentioned may be any material, provided that the synthesized nucleic acid (double-stranded) having a labelling substance introduced therein and the primer having a label introduced therein, or the synthesized nucleic acid (double-stranded) having a label introduced therein and the unit nucleic acid having a label introduced therein in the chain-extending reaction of the above primer can be easily separated from each other. As the material satisfying these conditions, adsorbents to be used for gel filtration or adsorbents to be used for ion-exchange may be conceivable. These adsorbents may be suitable particularly for separation of the synthesized nucleic acid having a label introduced therein and the unit nucleic acid having a label introduced therein, but are not necessarily preferable when the synthesized nucleic acid having a labelled substance introduced therein is separated from the primer having a label introduced therein. In the latter case, suitable materials may include hydroxyapatite and reversed phase system adsorbents such as silica gel derivatives, etc. Hydroxyapatite has been used in the prior art for separation of single-stranded DNA from double-stranded DNA, and only double-stranded DNA is adsorbed in low phosphate buffer, and when the concentration of phosphate buffer is increased, also double-stranded DNA is eluted {Y. Miyazawa, Thomas, C. A. (1965), J. Mol. Biol. 11, 223, M. McCallum, P. M. B. Walker (1967) Biochem. J. 105, 163}.

On the other hand, a silica gel derivative which is a solid adsorbent of the reversed phase chromatography, particularly octadecylsilane has been frequently utilized for high performance liquid chromatography, and can separate substances through difference in hydrophilic property or hydrophobic property. Whereas, when considered on nucleic acids, double-stranded DNA is more hydrophilic than single-stranded DNA, because bases are mutually hydrogen bonded, stacking occurs between the bases and futher the phosphoric diester is located outside of the double strand. Therefore, by use of the above silica gel derivative, for example, octadecylsilane, etc., single-stranded DNA can be easily separated from double-stranded DNA, wherein double-stranded DNA can be eluted first.

The solid adsorbent of the reversed phase chromatography mentioned here comprises silica gel, etc. to which a silane having a hydrocarbyl residue having 1 to 18 carbon atoms such as dimethylsilane, octadecylsilane, octylsilane, etc. is chemically bound, or a resin of small polarity such as a styrene-divinylbenzene copolymer or a gel filtration agent, etc. Also, by using optionally a device as shown in FIG. 1, a series of operations can be automated by combination with an instrument used in the already existing field of antibodies (e.g. plate washer). In this device shown, the solid adsorbent 2 is placed in a tip 1 having a taper by use of filters 3, 3.

d. Detection Method

In the case of separating the labelled synthesized nucleic acid (double-stranded) obtained in the chain-extending reaction of the primer from others having a label by use of a solid adsorbent, there are the two cases as shown below:

(i) the case where the labelled synthesized nucleic acid is eluted prior to others having a label (or the case when only the labelled synthesized nucleic acid is selectively eluted without adsorption on the solid adsorbent); (ii) the case where the labelled synthesized nucleic acid is eluted later than others having a label.

In the case of (i), the eluate which comes first is subjected as such, to measurement of the label contained in the solution, while in the case of (ii), after those having a label other than the labelled synthesized nucleic acid having been removed by thorough washing, the labelled synthesized nucleic acid may then be eluted, and subjected to the measurement of the label. When the labelling substance is a radioisotope, it is measured by use of a scintillator, or when it is a fluorescent or luminescent substance, by use of a known measurement method corresponding respectively thereto. When a plural number of objective nucleic acids is to be detected, measurement corresponding to the respective labelling substances can be performed with the use of the same sample (for example, when the respective labels are fluorescent substances with different fluorescent characteristics, excitation wavelength and fluorescent wavelength in conformity with the respective fluorescent substances may be selected).

Practically, by use of a receiver 5 or 5' as shown in FIG. 1, when the label is an isotope, an instrument such as Betaplate® (LKB), etc., and when the label is a fluorescent substance, an automatic fluorescence measuring device for microplate may be used. When the above receiver 5 or 5' is used, the above tip 1 filled with the solid adsorbent 2 may be mounted on a member 4 like microtiter well and used so as to place this over the receiver 5 or 5' as shown in the Figure. In the Figure, B indicates the case when the labelled synthesized nucleic acid (double strand) is eluted and A the case when the labelled primer or the labelled unit nucleic acid is eluted.

EXPERIMENTAL EXAMPLE

Example A-1

This example illustrates a method for detecting a β-galactosidase gene of *Escherichia coli*.

In *Escherichia coli* JM103 (Pharmacia Co.), β-galactosidase gene is partially deleted, so that it is possible to distinguish the deleted strain (JM103 in this case) and the wild strain [HB101 (BRL Co.) in this case] by performing extension reaction by the use of a primer corresponding to the part deleted. Thus, experiments for distinguishing the wild strain and the deletion strain were conducted by the following method.

The genes of *Escherichia coli* was extracted from JM103 and HB101 in accordance with the method described by L. Raymond et al. [Recombinant DNA Techniques pp. 45–46, Addison-Wesley Publishing Company (1983)]. The primer has a structure as shown below in which biotin (Bio) has been introduced in the 5'-terminal. An aminated oligonucleotide was synthesized with an automatic DNA synthesizer Model NS-1 (Shimadzu) and was then biotinylated with a succinimide ester of biotin (Japanese Patent Laid-Open Publication Nos. 93098/1984 and 93099/1984 which respectively correspond to U.S. Pat. Nos. 4,667,025 and 4,789,737 (Miyoshi et al.)):

(Bio)-GGGTTTTCCCAGTCACGACGTTGTA.

*Escherichia coli* which had been digested with a restriction enzyme EcoRI was added to a polymerase reaction solution [50 μl in total; 10% DMSO; 0.05 μg primer; 67 mM Tris-HCl, pH 8.8; 6.7 mM MgCl$_2$; 6.6 mM ammonium sulfate; 10 mM β-mercaptoethanol; 6.7 μM EDTA; 20 μM dATP; 20 μM dGTP; 20 μM TTP; 1 μM [α-$^{32}$P]dCTP (NEG-013H)]. The mixture was heated at 95° C. for 7 minutes and left standing at room temperature for 5 minutes, and a heat resistant DNA polymerase (0.5 U; New England Biolab) was added to the mixture to conduct the reaction at 50° C. for 10 minutes.

A streptavidin-agarose (BRL) as a fixative carrier was washed twice with a washing liquid (0.01M phosphate buffer, pH 7.2; 0.15M NaCl). Next, the aforementioned extension reaction mixture, 0.02M phosphate buffer, pH 7.2 and 0.3M NaCl (50 µl) were mixed together and added to the preliminarily treated streptavidin-agarose, and the mixture was left standing at room temperature for 30 minutes. After the reaction, the mixture was washed five times with the washing liquid (200 µl) to measure the radioactivity fixed on the streptavidin-agarose. As a result, the HB101 as a wild type in relation to the β-galactosidase gene and the JM103 as a deletion type could be successfully distinguished from each other.

Example A-2

This example illustrates a method for distinguishing a normal β-globin gene and a sickle cell anemia allele of β-globin.

As the normal β-globin gene and the β-globin gene of sickle cell anemia, the pBR322-HβPst and the pBR322-HβS which were the BamHI segments had respectively been inserted into a plasmid pBR322 were used [R. B. Wallace et al.: DNA, 3, 7–15 (1984)]. The primers have the structures as shown below and are complementary to different strands from each other. In one of the primers, the 5'-terminal was labelled with a polynucleotide kinase and a [γ-$^{32}$P]ATP, and the other was synthesized and biotinylated in the same manner as in Example A-1:

$^{32}$P-$^{5'}$ TTCTGACACAACTGTGTTCACTAGC$^{3'}$-    Primer A, (Bio)-$^{5'}$ACCACCAACTTCATCCACGTTCACC$^{3'}$-    Primer B.

A 10 ng portion of a plasmid (pBR322-HβPst or pBR322-HβS) which had been digested with a restriction enzyme EcoRI was added to a heat resistant DNA polymerase reaction solution [50 µl; 10% DMSO; 0.3 µg primer A; 0.3 µg primer B; 67 mM Tris-HCl, pH 8.8 in accordance with the protocol of New England Biolab Co.; 6.7 mM MgCl$_2$; 6.6 mM ammonium sulfate; 10 mM β-mercaptoethanol; 6.7 µM EDTA; 33 µM dATP; 33 µM dGTP; 33 µM dCTP; 33 µM dTTP]. The mixed solution was heated at 95° C. for 7 minutes, cooled down to room temperature and annealed for 5 minutes. Next, a heat resistant DNA polymerase (0.5 U; New England Biolab Co.) was added to the mixture to conduct the first extension reaction at 55° C. for 5 minutes. Then, the cycle of the denaturation at 91° C. for 1 minute—the annealing at room temperature for 5 minutes—the extension reaction at 55° C. for 5 minutes was repeated 20 times. To a streptavidin-agarose (50 µl) prepared in the same manner as in Example A-1 were added the reaction mixture (25 µl), water (75 µl) and 0.02M phosphate buffer, pH 7.2, 0.3M NaCl (100 µl), and the mixture was slowly stirred at room temperature to conduct the reaction for 30 minutes. The reaction mixture was washed 5 times with a washing liquor (200 µl). Then, the streptavidin-agarose was divided into two equivalent portions and poured into tubes respectively. To one of the tubes was added 100 µl of the reaction solution of a restriction enzyme DdeI [10 mM Tris-HCl (pH 7.5), 7 mM MgCl$_2$, 150 mM NaCl, 7 mM mercaptoethanol, 100 µg/ml calf serum albumin], and 5 µl of the restriction enzyme DdeI [Toyobo Co., Ltd., 10 U/µl] was added to the mixture. The reaction was performed with stirring slowly at 37° C. for 5 hours. After the reaction, the reaction mixture was washed 5 times with the washing solution (200 µl). Radioactivities remaining in the carrier before and after digestion with DdeI were measured for the plasmids pBR322-HβPst and pBR322-HβS, respectively, to evaluate the reduction of the radioactivity due to the DdeI digestion. As a result, the residual radioactivity after the DdeI digestion was 40% for pBR322-HβPst and 92% for pBR322-HβS, and thus these plasmids could be distinguished successfully.

Example A-3

This example illustrates the method for detecting simultaneously two kinds of genes in one sample.

Human β-globin gene and human papilloma virus 16 (HPV-16) were selected as the target genes. In order to amplify the β-globin gene, the following primers which were respectively complimentary to the dual strands of the β-globin gene, one of which was labelled with biotin and the other of which was fluorescence labelled with eocine isothiocyanate (EITC), were used:

Bio-NH-CAACTTCATCCACGTTCAAC(Bio-PG1),

EITC-NH-ACACAACTGTGTTCACTAGC(EITC-PG2).

In order to amplify the E6 gene of HPV-16, the following primers, one of which was labelled with biotin and the other of which was fluorescence-labelled with FITC, were used:

Bio-NH-TGAGCAATTAAATGACAGC(Bio-PVO1),

FITC-NH-TGTGCTTTGTACGCACAAC(FITC-PVO2).

As the samples to be detected, normal human placental gene and Caski cell (ATCC: CRL1550) were used. The former possesses the human globin gene but does not possess the papilloma virus gene. The latter is a cell derived from human being and naturally possesses the human globin gene, and it has been also clarified to possess the amplified gene of the human papilloma virus 16 [The EMBO Journal, 6, 139–144 (1987)].

Reaction 1:

The human placental gene (1 µg) and the primers [Bio-PVO1 (300 ng), FITC-PVO2 (300 ng), Bio-PG1 (300 ng) and EITC-PG2 (300 ng)] were added to a reaction solution [67 mM Tris-HCl, pH 8.8; 6.7 mM MgCl$_2$; 16.6 mM (NH$_4$)$_2$SO$_4$; 10 mM mercaptoethanol; 6.7 mM EDTA; 200 µM dATP, 200 µM dGTP; 200 µM dCTP; 200 µM TTP; 10% DMSO; total volume, 49 µl], and denaturation was performed at 95° C. for 5 minutes. After annealing at 55° C. for 1 minute, the Taq polymerase (NEB Co.; 2 U/µl; 1 µl) was added to the mixture, and the extension reaction was conducted at 70° C. for 2 minutes. Then, the denaturation was conducted at 92° C. for 1 minute and the annealing was conducted at 55° C. for 1 minute. The cycle of the denaturation, annealing and extension reaction was repeated 25 times.

Reaction 2:

Using a DNA (1 µg) obtained from the Caski cell, extension reaction was conducted with the same primer as the one in Reaction 1 in the same manner as in Reaction 1.

Preparation of streptavidin-agarose:

Streptavidin-agarose (BRL Co.) was preliminarily treated by washing twice with a washing solution (10 mM Tris-HCl, pH 7.5; 1 mM EDTA, pH 8.0; 0.1M NaHClO$_4$) and adding thereto salmon DNA (1 µg). A 20 µl portion of Reaction solution 1 or Reaction solution 2 was added to the preliminarily treated streptavidin-agarose (50 µl), and the mixture was left standing at room temperature for 15 minutes. After washing twice with the aforementioned washing solution (500 µl), the mixture was further washed twice with 1M NaHClO$_4$ (500 µl). It was then washed twice with the aforementioned washing solution (500 µl) and thrice with a solution [10 mM Tris-HCl, pH 7.5; 1 mM EDTA, pH 8.0; 50 mM NaCl] (500 μl). The DNA was denatured by adding 100 mM NaOH (50 μl) to obtain a supernatant, and a solution (10 mM Tris, pH 7.5; 1 mM EDTA, pH 8.0; 50 mM NaCl; 450 μl) was added to the supernatant to measure the fluorescence. The fluorescent measurement was conducted at the excitation wave length of 489 nm and the emission wave length of 520 nm for FITC, and at the excitation wave length of 520 nm and the emission wave length of 540 nm for EITC. The strength of each fluorescence was shown as a relative strength below:

|  | Reaction Solution 1 | Reaction Solution 2 |
| --- | --- | --- |
| Excitation wave length 489 nm Emission wave length 520 nm | 254 | 3,360 |
| Excitation wave length 520 nm Emission wave length 540 nm | 1,094 | 1,381 |

It can be judged from the above-described result that only the β-globin gene is present in normal human placental DNA, while both the β-globin gene and the papilloma gene are present in the Caski cell.

Example B-1

Separation of a single stranded DNA and a double stranded DNA was conducted with octadecylsilane (μBondapak $C_{18}$, Waters).

Sample 1:

The 5'-terminal of an oligodeoxynucleotide,

5'$_{HO}$-ACACAACTGTGTTCACTAGC was labelled with $T_4$ polynucleotide kinase and [γ-$^{32}$P]ATP.

Sample 2:

A plasmid from which fragments of 3,000 bp and 250 bp were obtainable upon digestion with the restriction enzyme Hind III was digested with Hind III, and both the terminals of each fragment were labelled with the Klenow fragment of E. coli DNA polymerase, [α-$^{32}$P]dCTP, dATP, dGTP and dCTP.

Sample 3:

Human placental DNA (1 μg); the oligodeoxynucleotide, $^{32}$P-ACACAACTGTGTTCACTAGC (300 ng), which was $^{32}$P-labelled in the same manner as in Sample 1, the oligonucleotide, $_{HO}$CAACTTCATCCACGTTCACC (300 ng) and Taq DNA polymerase (NEB Co.) were used to produce the β-globin gene partly amplified to each direction with the aforementioned two primers in accordance with the protocol of NEB.

Figure 2A:
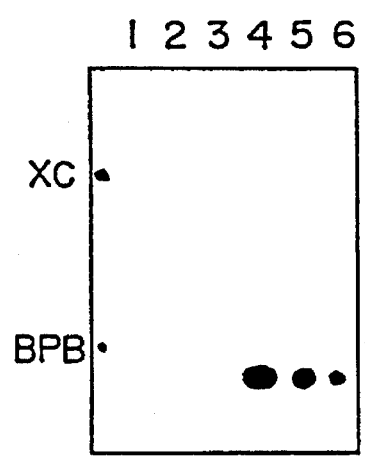
FIGS. 2A, B and C are sketches of the autoradiogram showing the result of separation of the β'-globin gene amplified by the PCR method from the nucleic acid (II)
Figure 2B:
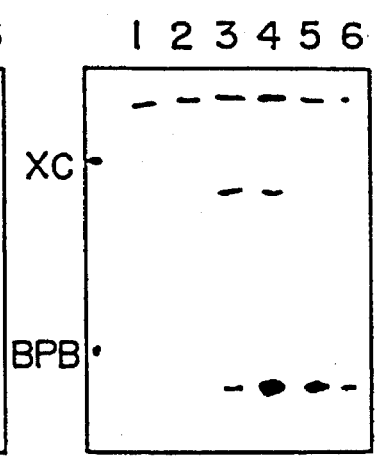
Figure 2C:
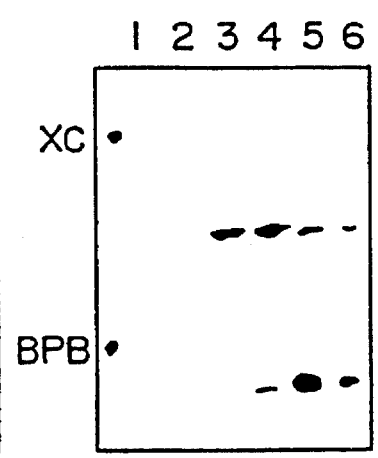

Siliconized glass wool was packed in a distal end of a pipette tip (1 ml volume) as shown in FIG. 1, the $C_{18}$ resin (100 μl) suspended in ethanol was added and washed with a solution for addition (50 mM NaCl, 10 mM Tris-HCl, pH 8.0; 0.1 mM EDTA, pH 8.0; 1 ml). To the tip was added 100 μl of each sample which had been prepared so that the concentration of NaCl was 50 mM. Furthermore, the solution for addition (500 μl) was added, and eluates were collected (Eluate 1). Next, the solution for addition containing 3% ethanol (500 μl) was added, and eluates were collected (Eluate 2). Subsequently, the elution was performed with increasing stepwise the ethanol concentration of the solution for addition. Eluate 3: 5% ethanol-solution for addition (500 μl); Eluate 4: 10% ethanol-solution for addition (500 μl); Eluate 5: 15% ethanol-solution for addition (500 μl); Eluate 6: 20% ethanol-solution for addition (500 μl). Each eluate was sampled in the equal amount, and the separation state was examined by the 5% polyacrylamide electrophoresis. The X-ray autoradiograms thus obtained are shown in FIG. 2. It was found from the analysis of Sample 1 that the single stranded DNA,

$^{32}$P-ACACAACTGTGTTCACTAGC was eluted with 10% ethanol-solution for addition (Eluate 4). It was also found from the analysis of Sample 2 that the double stranded DNA was eluted with 5% ethanol-solution for addition (Eluate 3). Moreover, it was also found from the analysis of Sample 3 that only the double stranded DNA synthesized by the DNA polymerase reaction was eluted with 5% ethanol-solution for addition (Eluate 3), and the synthesized double stranded DNA and the primers in small amounts were eluted with 10% ethanol-solution for addition (Eluate 4).

Example B-2

The behavior of a fluorescence-labelled oligodeoxynucleotide on a reversed phase adsorbent (octadecylsilane).

$^{32}$P-CAATTGACCCGGTTATTGC-NH$_2$,     Sample 1:

$^{32}$P-CAATTGACCCGGTTATTGC-NH-NBD,     Sample 2:

$^{32}$P-CAATTGACCCGGTTATTGC-NH-FITC.     Sample 3:

The synthesis and fluorescence labelling of an oligodeoxynucleotide having an amino group at the 3'-terminal were conducted in accordance with the methods disclosed in Japanese Patent Laid-Open Publication No. 166695/1985. The isotope labelling at the 5'-terminal was conducted in the same manner as in Example B-1 (Sample 1).

Figure 3A:
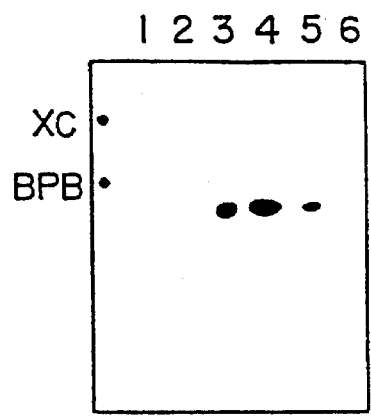
FIGS. 3A, B and C are sketches of the autoradiogram showing the behavior change of an oligonucleotide on the reversed phase adsorbent depending on the fluorescent material used.
Figure 3B:
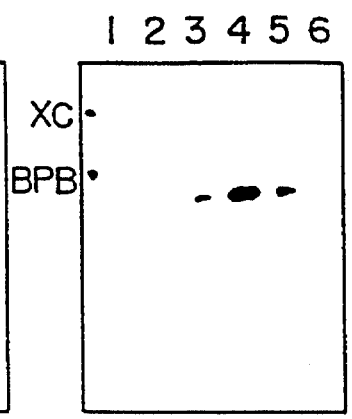
Figure 3C:
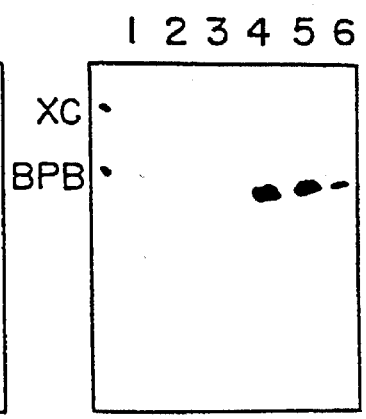

Experiment for examining the behavior of the oligodeoxynucleotide on a reversed phase adsorbent was conducted substantially in the same manner as in Example 1 by the use of Eluate 1: solution for addition (500 μl); Eluate 2: 5% ethanol-solution for addition (500 μl); Eluate 3: 10% ethanol-solution for addition (500 μl); Eluate 4: 15% ethanol-solution for addition (500 μl); Eluate 5: 20% ethanol-solution for addition (500 μl); Eluate 6: 30% ethanol-solution for addition (500 μl). The autoradiograms thus obtained are shown in FIG. 3. It was found from the result that the oligodeoxynucleotide in which a fluorescent label had been introduced was hardly eluted with 10% ethanol-solution for addition (Eluate 3) and such a tendency was particularly remarkable in the case of the FITC labelling (Sample 3).

Example B-3

The behavior of the oligodeoxynucleotide fluorescence-labelled at the 5'-terminal on a reversed adsorbent was examined by measuring fluorescence. The oligodeoxynucleotide having introduced in the 5'-terminal fluoresceine,

FITC-NH-ACACAACTGTGTTCACTAGC was synthesized in accordance with Japanese Patent Laid-Open Publication Nos. 93098/1984 and 93099/1984 which respectively correspond to U.S. Pat. Nos. 4,667,025 and 4,789,737 (Miyoshi et al.). It was placed in the reversed phase system and eluted in the same manner as in Example 2. The intensity of fluorescence of the eluates were measured with the excitation wave length of 489 nm and the emission wave length of 520 nm. The results are shown below:

| | Relative Intensity |
|---|---|
| Eluate 1 | 1 |
| Eluate 2 | 1 |
| Eluate 3 | 2 |
| Eluate 4 | 697 |
| Eluate 5 | 1,242 |
| Eluate 6 | 146 |

It was found from these results that the oligodeoxynucleotide fluorescence-labelled at the 5'-terminal was not eluted at all with 10% ethanol-solution for addition (Eluate 3).

Example B-4

Human β-globin gene was detected by the method for detecting genes by means of the extension reaction of a primer with a DNA polymerase.

Sample 1:

Human placental DNA (1 μg), FITC-NH-ACACAACTGTGTTCACTAGC (300 ng) and $_{HO}$CAACTTCATCCACGTTCAAC (300 ng) was added to a reaction solution containing no Taq DNA polymerase (prepared in accordance with the protocol of NEB Co., 100 μl in total).

Sample 2:

Gene amplification was conducted with Salmon sperm DNA (1 μg), FITC-NH-ACACAACTGTGTTCACTAGC (300 ng), $_{HO}$CAACTTCATCCACGTTCAAC (300 ng) and Taq DNA polymerase (NEB Co.) in accordance with the protocol of NEB Co. (number of amplification: 20; total volume: 100 μl).

Sample 3:

Gene amplification was conducted with Human placental DNA (1 μg), FITC-NH-ACACAACTGTGTTCACTAGC (300 ng), $_{HO}$CAACTTCATCCACGTTCAAC (300 ng) and Taq DNA polymerase (NEB Co.) in accordance with the protocol of NEB Co. (number of amplification: 20; total volume: 100 μl). The primers used in Samples 1–3 were the same combination of primers with each other and for the amplification of human β-globin gene.

A 450 μl portion of the solution for addition was added to 50 μl of each sample, and the mixture was added to a reversed phase resin prepared in the same manner as in Example B-1. After washing with the solution for addition (500 μl) and 5% ethanol-solution for addition (500 μl), elution was conducted with 10% ethanol-solution for addition (500 μl). To the eluate thus obtained was added 1M Tris-HCl (pH 9.5, 25 μl) to adjust the pH value to 8.5, and the measurement of fluorescence was performed at the excitation wave length of 489 nm and the fluorescence wave length of 520 nm. The results are shown below.

| | Sample 1 | Sample 2 | Sample 3 |
|---|---|---|---|
| Relative intensity | 3 | 30 | 111 |

It was found from the result that the β-globin gene in human DNA can be detected by means of this method.

Example B-5

The mutation of human β-globin gene was determined by the gene assay by means of the extension reaction of a primer with a DNA polymerase. A plasmid pBR322-HβS [Nucleic Acids Res., 9, 3647–3656 (1981)] having a gene whose β-globin gene had been point-mutated was used as a template, and a FITC-labelled primer completely complementary to the normal gene, FITC-NH-CACCTGACTCCTGAGGAGAAGT (F-GA); a primer completely complementary to a gene having a point mutation, FITC-NH-CACCTGACTCCTGTGGAGAAGT (F-GS); and a primer common to both the primers, $_{HO}$CAACTTCATCCACGTTCAAC (PG2) were used as the primers. As competitive primers, GS was used against F-GA and GA was used against F-GS.

Reaction 1:

pBR322-HβS (20 ng) having been digested with the restriction enzyme EcoRI, PG2 (300 ng), F-GA (300 ng) and GS (300 ng) were added to a reaction solution [67 mM Tris-HCl, pH 8.8; 6.7 mM MgCl$_2$; 16.6 mM (NH$_4$)$_2$SO$_4$; 10 mM β-mercaptoethanol; 6.7 mM EDTA; 200 μM dATP, 200 μM dGTP; 200 μM dCTP, 200 μM TTP; 10% DMSO] so as the total volume to be 49 μl, and the mixture was denaturated by heating at 95° C. for 5 minutes. After annealing at 65° C. for 1 minute, Taq polymerase (NEB Co., 20/μl, 1 μl) was added, and the extension reaction of the primers was conducted at 73° C. for 2 minutes. Next, the mixture was denaturated at 92° C. for 1 minute and annealed at 65° C. for 1 minute. Subsequently, the cycle of the denaturation, annealing and extension reaction was repeated 20 times in the same manner as above.

Reaction 2:

Extension reaction was repeated 20 times under the same reaction condition as in Reaction 1 with pBR322-HβS digested with Eco RI (20 ng), PG2 (300 ng), F-GS (300 ng) and GA (300 ng).

The solution for addition (450 ng) was added to each of the reaction solution (50 μl), and the mixture was added to a reversed phase resin prepared in the same manner as in Example B-1. Elution was conducted with 10% ethanol-solution for addition (500 μl) in the same manner as in Example B-4. To the eluate was added 1M Tris-HCl (pH 9.5, 25 μl) to adjust the pH value to 8.5, and the measurement of fluorescence was conducted at the excitation wave length of 489 nm and the emission wave length of 520 nm. Results are shown below.

| | Reaction 1 | Reaction 2 |
|---|---|---|
| Relative intensity | 45 | 132 |

From these results, it could be judged that an extension reaction product was produced in preponderantly larger amount in Reaction 2 than in Reaction 1 and thus it could be judged that the plasmid pBR322-HβS was the one that point mutation was caused in the globin gene.

Figure 4:
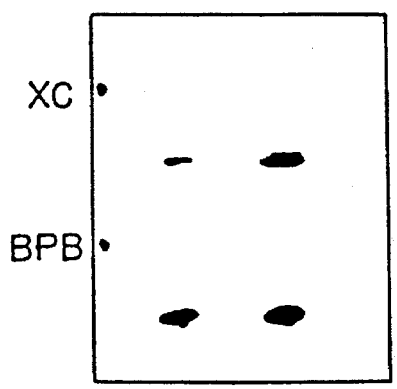
FIG. 4 is a sketch of the autoradiogram discriminating the point mutation by the PCR reaction.

In order to confirm the aforementioned result, F-GA or F-GS in Reaction 1 or 2 was labelled with $^{32}$P, and the extension reaction was conducted in the same manner [Reaction 3: pBR322-HβS (20 ng), $^{32}$P-GA (300 ng), GS (300 ng); Reaction 4: pBR322-HβS (20 ng), $^{32}$P-GA (300 ng), GA (300 ng)]. Reaction solutions thus obtained were analyzed by 5% polyacrylamide electrophoresis (FIG. 4). An extension reaction product was obtained mainly in Reaction 4, which coincided with the results of Reactions 1 and 2.

INDUSTRIAL APPLICABILITY

The method of detecting an intended nucleic acid in a sample will make it possible to detect a specified nucleic acid without resort to what is called hybridization method which is complicated. Furthermore, a plurality of intended nucleic acids can be detected at the same time. Accordingly the method in recordance with the present invention can be widely utilized in diagnosis of genopathy before birth and of cancer at the molecular level, or detection of pathogens such as viruses.

What is claimed is:

1. A method of detecting the presence or absence of an objective nucleic acid in a sample, wherein the objective nucleic acid is a single-stranded or double-stranded DNA, which method comprises:

A) where the objective nucleic acid is a double-stranded DNA, subjecting the sample to denaturing conditions which disintegrates the double-stranded DNA into two single strands, B) amplifying a DNA sequence of the objective nucleic acid in the sample by subjecting the sample to a DNA polymerase chain extension reaction, the objective nucleic acid being either the single-stranded DNA when the objective nucleic acid is single-stranded or being one of the two single strands obtained in step A) when the objective nucleic acid is double-stranded, said amplifying step comprising a step (i) of forming a double stranded product characterized in using said DNA sequence as a template, four unit mono-deoxyribonucleotidetriphosphates having no label for detection and a pair of single-stranded primer nucleic acids that are shorter than the template but are long enough to specifically hybridize with the template, solely a first member of the primer pair having a label for detection and solely a second member of the primer pair having an added site capable of specifically binding with an added site on a solid carrier or support, the double-stranded product being composed of the template and a synthesized nucleic acid complementary to the template formed from the first or second members of the primer pair, a step (ii) of disintegrating the double-stranded product of the step (i) into two single strands and a step (iii) of repeating the steps (i) and (ii) wherein at least one of the single strands obtained in step (ii) is used as the template and the step (ii) is omitted in a final cycle, thereby obtaining an amplified product of said DNA sequence, which product has a double stranded structure and contains both the added site capable of specifically binding with the added site on the solid carrier or support as well as the label for detection;

C) contacting the sample obtained in step B) with the solid carrier or support under conditions wherein the added site of the amplified product specifically binds with the added site on the solid carrier or support, to immobilize the amplified product onto the solid carrier or support;

D) separating the solid carrier or support having the amplified product immobilized thereon from the rest of the sample; and E) subjecting the solid carrier or support having the amplified product immobilized thereon to a process for detection of the label for detection contained in the amplified product, to thereby determine whether there is the label for detection on the solid carrier or support and to thereby detect the presence or absence of the objective nucleic acid in the sample.

2. The method as claimed in claim 1, wherein the added site capable of specifically binding with the added site on the solid carrier or support and the label for detection of the respective first and second members of the pair of primer nucleic acids are different from each other.

3. The method as claimed in claim 1, wherein the label for detection or the added site capable of specifically binding with the added site on the solid carrier or support is chemically bound to a hydroxyl group at the 5' terminus of the respective first or second members of the primer pair.

4. The method as claimed in claim 1, wherein the label for detection or the added site capable of specifically binding with the added site on the solid carrier or support is present at the base moiety of or the phosphodiester moiety of the respective first or second members of the primer pair.

5. The method as claimed in claim 1, wherein the amplified product is immobilized onto the solid carrier or support through a non-covalent bond between the added site capable of specifically binding with the added site on the solid carrier or support contained in the amplified product and the added site on the solid carrier or support.

6. The method as claimed in claim 1, wherein the label for detection is radioactive, fluorescent or chemiluminescent.

7. The method as claimed in claim 1, wherein the label for detection is a hapten or a ligand for a receptor.

8. The method as claimed in claim 7, wherein the ligand for a receptor is biotin.

9. The method as claimed in claim 1, wherein the added site capable of specifically binding with the added site on the solid carrier or support comprises a hapten or a ligand for a receptor.

10. The method as claimed in claim 9, wherein the ligand for a receptor is biotin.

11. A pair of single-stranded primer nucleic acids for use in a DNA polymerase chain extension reaction method using an objective single-stranded nucleic acid as a template, wherein the primer nucleic acids are shorter than the template but are long enough to specifically hybridize with the template, solely a first member of the primer pair having a label for detection and solely a second member of the primer pair having an added site capable of specifically binding with an added site on a solid carrier or support, the added site capable of specifically binding with the added site on the solid carrier or support being different from the label for detection.

12. The primer pair as claimed in claim 11, wherein the label for detection or the added site capable of specifically binding with the added site on the solid carrier or support is chemically bound to a hydroxyl group at the 5' terminus of the respective first or second members of the primer pair.

13. The primer pair as claimed in claim 11, wherein the label for detection or the added site capable of specifically binding with the added site on the solid carrier or support is present at the base moiety of or the phosphodiester moiety of the respective first or second members of the primer pair.

14. The primer pair as claimed in claim 11, wherein second member of the primer pair of the nucleic acids is bound on the solid carrier or support through a non-covalent bond between the added site capable of specifically binding with the added site on the solid carrier or support contained in the nucleic acid and the added site on the solid carrier or support.

15. The primer pair as claimed in claim 11, wherein the label for detection is radioactive, fluorescent or chemiluminescent.

16. The primer pair as claimed in claim 11, wherein the label for detection is a hapten or a ligand for a receptor.

17. The primer pair as claimed in claim 11, wherein the ligand for a receptor is biotin.

18. The primer pair as claimed in claim 11, wherein the added site capable of specifically binding with the added site on the solid carrier or support comprises a hapten or a ligand for a receptor.

19. The primer pair as claimed in claim 18, wherein the ligand for a receptor is biotin.

* * * * *